United States Patent [19]

Grosso et al.

[11] 4,128,726
[45] Dec. 5, 1978

[54] PROCESS FOR THE PREPARATION OF ARYL ESTERS OF 3,5-DI-T-BUTYL-4-HYDROXYBENZOIC ACID

[75] Inventors: Vincent G. Grosso, New City, N.Y.; Ray L. Hillard, Annandale, N.J.

[73] Assignee: American Cyanamid Company, Stamford, Conn.

[21] Appl. No.: 863,378

[22] Filed: Dec. 22, 1977

[51] Int. Cl.$^2$ .............................................. C07C 69/76
[52] U.S. Cl. .................................................. 560/72
[58] Field of Search ........................................ 560/72

[56] References Cited

U.S. PATENT DOCUMENTS

| 3,112,338 | 11/1963 | Smutny et al. | 260/473 |
|---|---|---|---|
| 3,496,211 | 2/1970 | Dexter et al. | 560/67 |
| 3,591,553 | 7/1971 | Lappin et al. | 260/473 |
| 3,681,431 | 8/1972 | Dexter et al. | 560/67 |
| 3,988,471 | 10/1976 | Kohn et al. | 560/67 |
| 4,038,250 | 7/1977 | Lind | 560/72 |

*Primary Examiner*—Paul J. Killos
*Attorney, Agent, or Firm*—Frank M. Van Riet

[57] ABSTRACT

Aryl esters of 3,5-di-t-butyl-4-hydroxybenzoic acid are produced by reacting 3,5-di-t-butyl-4-hydroxybenzoic acid with a hydroxyphenol in the presence of di-n-butylether as a non-reactive, organic solvent.

4 Claims, No Drawings

PROCESS FOR THE PREPARATION OF ARYL ESTERS OF 3,5-DI-T-BUTYL-4-HYDROXYBENZOIC ACID

BACKGROUND OF THE INVENTION

The use of aryl esters of 3,5-dit-t-butyl-4-hydroxybenzoic acid as light stabilizers for polyolefins, particularly polypropylene, is taught in U.S. Pat. No. 3,112,338. These esters have become increasingly useful as light stabilizers, although processes for their manufacture have not proven to be as commercially attractive as would be desired.

Smutny el al. U.S. Pat. No. 3,112,338, at col, 1, lines 63–71 and in Examples I and II, teach the production of these esters by heating substantially equimolar amounts of 3,5di-tert.butyl-4-hydroxybenzoyl cloride and 2,4-di-tert.butylphenol on a steam bath until molten, resolidifying them and then recrystallizing from Skelly B or ether in 70% yield. This process, due to its low yield, is not suitable for commercial manufacture.

Reaction in a solvent system is also known. Lappin et al., U.S. Pat. No. 3,591,553, teach a process wherein an analogous esterification of 4-hydroxyisophthalic acid with phenols is disclosed. In this process, the acid, an alkylphenol and a condensing agent (phosphoryl chloride, also known as phosphorus oxychloride) are reacted in a hydrocarbon solvent such as toluene, benzene, hexane, heptane etc. However, the reactants (primarily the benzoic acid compound) are not readily soluble in these solvents and productivity using them is poor.

Accordingly, if a process could be found which would enable the production of aryl esters of 3,5-di-t-butyl-4-hydroxybenzoic acid in higher yields and of high quality, a long felt need would be satisfied.

SUMMARY

It has now been found that aryl esters of 3,5-di-t-butyl-4-hydroxybenzoic acid can be produced at higher yields by using di-n-butyl ether as the reaction solvent. This solvent enables the production of the aryl esters in commercial quantities since the initial reactants are all soluble therein while the product aryl esters are not.

Although the di-n-butyl ether has been found to be useful in the instant process, not all oxygenated materials so function. Butyl acetate, for example, affords good yields of product aryl ester but is partially lost itself in the process due to either hydrolysis or transesterification.

DESCRIPTION OF THE INVENTION INCLUDING PREFERRED EMBODIMENTS

There has now been found a process for the preparation of aryl esters of 3,5-di-t-butyl-4-hydroxybenzoic acid having the formula

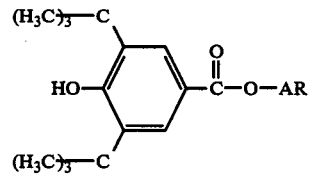

wherein AR represents a mono-aromatic ring substituted with an aryl group of from 1–4 carbon atoms.

The process comprises reacting a compound having the formula

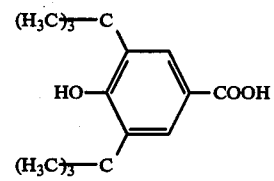

with a phenol having the formula

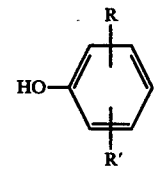

wherein R and R' are, individually, hydrogen or a lower alkyl of 1–4 carbon atoms, inclusive, at least one of R and R' being alkyl.

Phosphonyl chloride is employed as the chlorinating agent whereby the 3,5-di-t-butyl-4-hydroxybenzoic acid is converted to the benzoyl chloride which then reacts with the phenol to form the ester, eliminating hydrogen chloride. The reaction is conducted in the presence of di-n-butyl ether as the solvent.

Essentially, equimolar quantities of the acid, phenol and phosphorus oxychloride are reacted together. A slight excess of phenol over the amount of acid may be used, e.g., about a 10% excess. The amount of phosphorus oxychloride used is essentially equivalent in moles to the number of moles of the acid.

The reactants are heated in the di-n-butyl ether at a temperature of 70°–80° C. for a suitable period of time (4–8 hours or more) with elimination of hydrogen chloride. An HCl scrubber is preferably used. When the reaction is completed (cessation of HCl formation), the reaction mixture is cooled to about normal room temperature and washed with water to remove residual hydrogn chloride, each time discarding the aqueous wash. Then, the organic reaction mixture is drowned into methanol to destroy excess phosphorus oxychloride. The methanolic solution may be facilitated by warming to 60°–70° C. The product is isolated by cooling of the solution to 0° to −5° C., filtering the crystals and washing with methanol and water.

The advantages attained by the use of the di-n-butyl ether as the solvent in the present process include (1) improved yield, (2) improved purity without the need for further purification, (3) improved color and (4) solvent recoverability.

Examples of phenols represented by the above formula and useful as charge materials in the instant process include, o, m or p-methyl, ethyl, propyl or butyl phenol, 1,2-dimethyl phenol, 1,3-diethyl phenol, 1,4-dimethyl phenol, 1,5-dipropyl phenol, 2,3-di-n or t-butyl phenol, 2,4-dimethyl phenol, 2,5-diethyl phenol and the like. The preferred phenol is 2,4-di-t-butylphenol.

The following examples are set forth for purposes of illustration only and are not to be construed as limitations on the present invention except as set forth in the appended claims. All parts and percentages are by weight unless otherwise specified.

EXAMPLE 1

14.0 Parts of di-n-butyl ether, 18.0 parts of 3,5-di-tert-butyl-4-hydroxybenzoic acid, 15.0 parts of 2,4-di-tert-butylphenol and 7.0 parts of phosphorus oxychloride are charged to a suitable glass-lined reactor fitted with a scrubber for hydrogen chloride gas. The reaction mixture is heated to 75°–80° C., stirred at this temperature for about 5 hours and then cooled to about 20° C. The reaction mixture is then washed several times with water to remove residual hydrogen chloride, each time discarding the water wash. The organic phase is then drowned into methanol, warmed to 65°–70° C. and the solution cooled to 0 to −5° C. to crystallize the product. The crystals are centrifuged, washed with methanol, then water, and dried. Yield of 2,4-di-t-butylphenyl-3,5-di-t-butyl-4-hydroxybenzoate is about 83% of theoretical. The di-n-butyl ether is readily recovered by distillation.

EXAMPLE 2

The procedure of Example 1 is again followed except that the phenol is replaced by an equivalent amount of p-methyl phenol. Substantially equivalent results are obtained.

EXAMPLE 3

Again, following the procedure of Example 1, except that the phenol is replaced by an equivalent amount of 1,3-dipropyl phenol, analogous results are observed.

EXAMPLE 4

When the procedure of Example 1 is again followed, except that an equivalent amount of 2,4-diethyl phenol is used, the results are again substantially the same.

EXAMPLE 5

(Comparative)

28.0 Parts of n-butyl acetate, 18.0 parts of 3,5-di-tert-butyl-4-hydroxybenzoic acid, 15.0 parts of 2,4-di-tert-butylphenol and 7.0 parts of phosphorus oxychoride are charged to a suitable glass-lined reactor equipped with an HCl scrubber. The reaction mixture is heated to 75°–80° C., stirred at this temperature for about 5 hours and cooled to about 20° C. The mixture is then neutralized by the addition of 20% aqueous soda ash, cooled and filtered. The product is extremely difficult to filter and wash using a conventional cloth-lined whizzer, due to very fine particle size and to insoluble salts from the neutralization. The product contains a high (0.3%) insoluble content, requiring reslurry in water, a second filtration, and washing with water and methanol. This treatment reduces overall yield to about 60% of theoretical.

EXAMPLE 6

(Comparative)

When the product reaction mixture of Example 5 is drowned in methanol to destroy phosphorus oxychloride without prior neutralization, the n-butylacetate transesterifies with methanol producing methylacetate resulting in a loss of solvent.

We claim:

1. In a process for the preparation of compounds having the formula

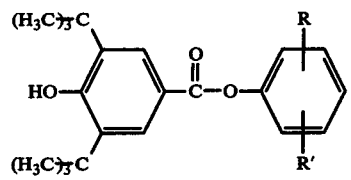

wherein R and R' are, individually, hydrogen or lower alkyl of 1–4 carbon atoms, inclusive, at least one of R and R' being alkyl, whereby 3,5-di-t-butyl-4-hydroxybenzoic acid is reacted with a phenol having the formula

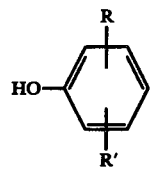

wherein R and R' are as defined above in the presence of phosphorus oxychloride, the improvement which comprises conducting the reaction in the presence of a non-reactive organic solvent comprising di-n-butyl ether.

2. A process according to claim 1, wherein R is hydrogen and R' is alkyl.

3. A process according to claim 1 wherein both R and R' are alkyl.

4. A process according to claim 1 wherein both R and R' are t-butyl.

* * * * *